US012751919B2

(12) United States Patent
Oefelein et al.

(10) Patent No.: US 12,751,919 B2
(45) Date of Patent: Oct. 6, 2026

(54) LIPOSOMAL ENHANCED INTRA-PERITONEAL CHEMOTHERAPY

(71) Applicant: TESORX PHARMA, LLC, Menlo Park, CA (US)

(72) Inventors: Michael G. Oefelein, Tustin, CA (US); Natarajan Venkatesan, Diamond Bar, CA (US); Nitin K Swarnakar, Chino Hills, CA (US); Teresa B. Hong, El Monte, CA (US); Guru V. Betageri, Chino Hills, CA (US); Ramachandran Thirucote, Altherton, CA (US); Lining Zhu Hutchinson, Duarte, CA (US)

( * ) Notice: Subject to any disclaimer, the term of this patent is extended or adjusted under 35 U.S.C. 154(b) by 1118 days.

(21) Appl. No.: 17/290,329

(22) PCT Filed: Nov. 4, 2019

(86) PCT No.: PCT/US2019/059655
§ 371 (c)(1),
(2) Date: Apr. 30, 2021

(87) PCT Pub. No.: WO2020/093044
PCT Pub. Date: May 7, 2020

(65) Prior Publication Data

US 2022/0000777 A1 Jan. 6, 2022

Related U.S. Application Data

(60) Provisional application No. 62/755,026, filed on Nov. 2, 2018.

(51) Int. Cl.

| | |
|---|---|
| ***A61K 9/127*** | (2025.01) |
| ***A61K 31/337*** | (2006.01) |
| ***A61K 33/42*** | (2006.01) |
| ***A61K 47/24*** | (2006.01) |
| ***A61P 35/00*** | (2006.01) |

(52) U.S. Cl.
CPC ............ *A61K 9/127* (2013.01); *A61K 31/337* (2013.01); *A61K 33/42* (2013.01); *A61K 47/24* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 4,128,173 A * | 12/1978 | Lazarus | A61B 17/3415 206/362 |
| 8,642,074 B2 * | 2/2014 | Mei | A61K 9/127 514/492 |
| 2007/0190182 A1 * | 8/2007 | Pilkiewicz | A61K 9/127 514/184 |
| 2009/0130193 A1 | 5/2009 | Pilkiewicz et al. | |
| 2015/0174263 A1 | 6/2015 | Sengupta et al. | |
| 2016/0000650 A1 * | 1/2016 | Gobbi Frattini | B65D 81/3216 604/408 |

FOREIGN PATENT DOCUMENTS

| | | | | |
|---|---|---|---|---|
| JP | H10509459 A | 9/1998 | |
| JP | 2006525368 A | 11/2006 | |
| JP | 2015098498 A | 5/2015 | |
| JP | 2018505224 A | 2/2018 | |
| JP | 2018528933 A | 10/2018 | |
| WO | 1994026253 A1 | 11/1994 | |
| WO | 1996015774 A1 | 5/1996 | |
| WO | 2004098524 A2 | 11/2004 | |
| WO | 2006055352 A2 | 5/2006 | |
| WO | 2013012891 A1 | 1/2013 | |
| WO | 2016134066 A1 | 8/2016 | |
| WO | WO-2016131006 A1 * | 8/2016 | A61K 31/337 |
| WO | WO-2017120586 A1 * | 7/2017 | A61K 31/337 |
| WO | 2018/089759 A1 | 5/2018 | |

OTHER PUBLICATIONS van Driel et al. "Hyperthermic Intraperitoneal Chemotherapy in Ovarian Cancer", The New England Journal of Medicine, Jan. 18, 2018, 378, 230-240. (Year: 2018).*
Thoracic Key "Mechanical Complications of Peritoneal Dialysis" Jul. 18, 2017 https://thoracickey.com/mechanical-complications-of-peritoneal-dialysis/ (accessed Feb. 27, 2024). (Year: 2017).*
Extended European Search Report for No. PCT/US2019/059655, dated Jun. 22, 2022.
Zhigaltsev et al., "Development of a weak-base docetaxel derivative that can be loaded into lipid nanoparticles," Journal of Controlled Release, vol. 144, Issue 3, Jun. 15, 2010, pp. 332-340.
International Search Report and Written Opinion in International Application No. PCT/US2019/059655, dated Jan. 24, 2020.
Preliminary Report on Patentability in International Application No. PCT/US2019/059655, dated May 14, 2021.
"Epithelial ovarian cancers," Target Ovarian Cancer, Jun. 2018 (Jun. 2018) first paragraph (retrieved Dec. 20, 2019 (Dec. 30, 2019) via the internet at <https://www.targetovariancancer.org.uk/information-and-support/what-ovarian-cancer/typesovarian-cancer/epithelial-ovarian-cancers>].

(Continued)

*Primary Examiner* — Bethany P Barham
*Assistant Examiner* — Judith Marie Kamm
(74) *Attorney, Agent, or Firm* — Raphael Bellum PLLC

(57) ABSTRACT

Methods for-treating neoplasms by intraperitoneally administering liposomal formulations of chemotherapeutic drugs are disclosed. The methods include methods of instilling liposomal formulations of taxane and platin chemotherapeutic agents into the peritoneal cavity of a subject to treat ovarian cancer or a primary peritoneal cancer are disclosed. The liposomal formulations include (a) a taxane (e.g., paclitaxel or docetaxel) or platin, (b) a first phospholipid, dipalmitoyl phosphatidylcholine (DMPC), and (c) a second phospholipid, dimyristoyl phosphatidyl glycerol sodium (DMPG).

14 Claims, 4 Drawing Sheets

(56) References Cited

OTHER PUBLICATIONS

"Pseudomyxoma peritonei (PMP)", Macmillan Cancer Support, Mar. 31, 2016 (Mar. 31, 2016) para 2 [retrieved Dec. 20, 2019 (Dec. 30, 30, 2019) via the internet at <https://www.macmillan.org.uk/information-and-support/pseudomyxoma-peritonei-pmp>].
"Peritoneal Cancer", WebMD, Mar. 13, 2019 (Mar. 13, 2019) para 3 [retrieved Dec. 20, 2019 (Dec. 30, 2019) via the Internet at <https://www.webmd.com/cancer/peritoneal-cancer-prognosis-symptoms-treatments#1>].
"Cisplatin", Wikipedia, Dec. 21, 2016 (Dec. 21, 2016) first paragraph [retrieved Jan. 6, 2020 (Jan. 1, 2020) via the internet at <https://en.wikipedia.org/wiki/Cisplatin>].

* cited by examiner

LIPOSOMAL ENHANCED INTRA-PERITONEAL CHEMOTHERAPY

FIELD OF THE INVENTION

The field of this invention relates to the treatment of ovarian and peritoneal neoplasms.

BACKGROUND

In 2014 there were 21,980 new cases of ovarian cancer detected in the United States, and 65,697 cases detected in the European Union. As no simple screening test is available to detect ovarian cancer, only 15% of women suffering from ovarian cancer present with localized disease. There are also other major challenges to treating ovarian cancer, including the fact that around 80% of ovarian cancer patients develop drug resistance during therapy.

In general, the standard of care for ovarian cancer has remained largely unchanged since the 1970s. While conventional optimal surgery and adjuvant paclitaxel-carboplatin chemotherapy can increase survival, 70% of patients that have undergone that regimen relapse within 3 years. Alternative therapeutic options, including: the angiogenesis inhibitor, Bevacizumab (Avastin®); inhibitors of poly ADP ribose polymerase ("PARP"), such as Olaparib (Lynparza®), rucaparib (Rubraca®), and niraparib (Zejula®); and cyto-reductive surgery ("CRS") plus adjuvant chemotherapy (platinum-based plus paclitaxel) have also not proven to be reliably successful in the long-term, and are not free from quality of life-lowering side effects and high costs. Thus, there is an urgent need for more ovarian cancer therapies.

Stage III ovarian cancer has the highest mortality of all gynecological cancers. The conventional therapy for stage III ovarian cancer is CRS and six cycles of intravenous ("IV") paclitaxel carboplatin/chemotherapy or, alternatively, CRS performed after 3 cycles of IV chemotherapy. However, Intraperitoneal delivery of chemotherapy has been demonstrated to enhance drug delivery at the peritoneal surface and improve overall survival by eliminating microscopic peritoneal disease more efficiently than IV chemotherapy. Indeed, the peritoneal surfaces is the primary site of disease recurrence after standard treatments for ovarian cancer, and combination treatment with IV and intraperitoneal chemotherapy has been shown to prolong overall survival after primary CRS in patients with stage III ovarian cancer. However, peritoneal catheter related problems associated with intraperitoneal delivery of chemotherapy increases demands on the patient. Specifically, gastro-intestinal and renal side effects hamper the adoption of intraperitoneal installation.

Nevertheless, on the basis of the results of three multicenter randomized Phase 3 clinical trials intraperitoneal chemotherapy has now been shown to be superior to standard IV chemotherapy and primary chemotherapeutic management of small volume residual advanced epithelial ovarian cancer. The barriers to implementation of this treatment and to its implementation in clinical practice appears to be toxicity concerns, as well as the lack of technical expertise with the peritoneal infusion device.

Dietrich et al. in 1978 published manuscript that presents a theoretical modeling study supporting the examination of intraperitoneal antineoplastic drug delivery as a management strategy for ovarian cancer, suggesting that tumor present within the peritoneal cavity could be exposed to cytotoxic drug concentrations 1 to several logs greater with regional treatment than could be safely obtained with systemic drug administration. Early Phase 1 clinical studies confirm the fact that the peritoneal cavity could be exposed to substantially greater concentrations of cytotoxic agents with known activity and ovarian cancer, for example 10-20 fold for cisplatin and carboplatin and greater than 1000 fold for paclitaxel) than possible with systemic therapy delivery. Subsequently-conducted Phase 2 trials, the majority of which were cisplatin based, revealed that a proportion of patients with small volume residual ovarian cancer could achieve a surgically-documented complete response after second line intraperitoneal chemotherapy when this clinical state had not been achieved in the same individual after primary platinum based chemotherapy. Furthermore, an intraperitoneal cisplatin regimen was associated with a statistically significant improvement in overall survival median 49 versus 41 months (p=0.02).

Paclitaxel has also been tested for intraperitoneal use in a Phase 1 study, in which the dose-limiting toxicity was abdominal pain. A second intraperitoneal paclitaxel trial demonstrated the improved tolerability of the lower dose weekly regimen. In a subsequently conducted Phase 3 study using intraperitoneal paclitaxel (60 mg/m$^2$ per week for 16 weeks) in women with a positive second look laparotomy and less than 0.5 cm residual tumor nodules, 61% of microscopic residual patients achieved a surgical complete response. Only one of the 31 women with macroscopic residual cancer experienced a complete response.

In another Phase 3 trial exploring intraperitoneal cisplatin-based therapy and the addition of intraperitoneal paclitaxel consisted of day 1 intravenous paclitaxel (135 mg/m$^2$) administered during 24 hours, day 2 intraperitoneal cisplatinum (100 mg/m$^2$), and day 8 intraperitoneal paclitaxel (60 mg/m$^2$). The control arm and this study was standard 24 hour IV infusion of paclitaxel (135 mg/m$^2$) and day 2 IV cis-platinum (75 mg/m$^2$). The intraperitoneal treatment regimen resulted in a highly statistically significant improvement in both progression free (median, 24 versus 18.3 months; p=0.027), and overall survival (median, 65.6 versus 49.7 months; p=0.017). However, the intraperitoneal program was associated with more toxicity, resulting in myelosuppression, emesis, neuropathy, and abdominal discomfort. This study also included a formal quality of life analysis a 12 month follow-up, which showed there was no difference in quality of life between the 2 treatment gluteal groups, although patients receiving intraperitoneal therapy experienced a greater short-term decline in the in quality of life compared with systemic drug delivery.

Delivery of the intraperitoneal chemotherapy at the end of surgery can circumvent most of these drawbacks while maintaining its advantages. With that though in mind, hyperthermic intraperitoneal chemotherapy ("HIPEC) was evaluated in a Phase 3 trial, which demonstrated an overall survival advantage in patients with stage III ovarian cancer undergoing cytoreductive surgery with, and without, Hypaque®. (van Driel W J et al.) In that trial perfusion with cisplatin at a dose of 100 mg/m$^2$ at a flow rate of 1 L/min was used, and the perfusate was heated to 40° C. In total, HIPEC procedure adds 120 minutes in total to the CRS operation.

In addition to convenience, advantages of a single HIPEC procedure during surgery also include an overall survival time of 11.8 months over CRS alone plus neoadjuvant intravenous chemotherapy. HIPEC also had little effect on safety in the incidence of postoperative complications, the incidence of Grade 3 or 4 adverse events, and health-related quality of life outcomes did not differ significantly between the surgery plus HIPEC group and the surgery group.

In view of the advantages offered by HIPEC over other standard treatment regimens for ovarian cancer, this disclosure describes liposomal enhanced intraperitoneal chemotherapy ("LEIPC") as an alternative approach for delivering chemotherapy via intraperitoneal instillation to treat ovarian and peritoneal cancers like pseudomyxoma peritonei. LEIPC employs specialized liposomal formulations of chemotherapeutic drugs, such as, but not limited to, paclitaxel, docetaxel, and cisplatin, improve penetration and enhance tolerability of intraperitoneal instillation of chemotherapy. Advantages of LEIPC over HIPEC and conventional ovarian cancer therapies include improved progression-free survival and overall success, while shortening the time a patient spends in the operating room. LEIPC is also better-tolerated by patients than HIPEC, and because LEIPC instillation can be performed using a ready to use closed package system, it avoids the need to coordinate therapy with a medical oncologist or pharmacist.

SUMMARY

The invention described herein is directed to treating neoplasms by intraperitoneal administration of liposomal formulations of chemotherapeutic drugs. Accordingly, in embodiments of the invention, a liposomal formulation of a chemotherapeutic drug is intraperitoneally-admininistered to a subject, in need thereof, via, for example, instillation of the liposomal formulation into the peritoneal cavity, to treat a neoplasm. In preferred embodiments, a method and composition of the invention is be used to treat an ovarian cancer or primary peritoneal cancer, such as pseudomyxoma peritonei ("PMP").

The liposomal formulations of chemotherapeutic drugs that are administered in accordance with the invention are typically prepared by hydrating proliposomal powder dispersions of a chemotherapeutic drug and one or more lipid components, as described in U.S. patent application Ser. Nos. 16/066,836 and 16/348,801, and their respective corresponding PCT applications, WO 2018/089759 and WO 2017/120586, which are all incorporated herein in its entirety. Advantages offered by liposomal formulations of the invention over conventional chemotherapies include increased post-instillation dwell times and improved delivery of the chemotherapeutic drugs to neoplasm targets.

In various embodiments, liposomes according to the invention are composed of a chemotherapeutic agent, such as, for example, a taxane or platin drug, a first phospholipid component and a second phospholipid component. In a preferred embodiment of the invention, the liposomal formulation includes paclitaxel, DMPG and DMPC in w/w/w ratios of (1):(1.43):(0.567), which are to be understood herein as also including approximates of the foregoing ratios, including, for example, (1):(1.4):(1.6) or (1):(1.4):(1.567).

Methods and compositions of the present invention can also be adapted into kits, which for example can take the form of a closed package systems that reduce the complexity and personnel requirements associated with conventional chemotherapy delivery protocols.

BRIEF DESCRIPTION OF THE FIGURES

FIG. 1A shows a dosage curve for the TSD-001 paclitaxel liposomal formulation against cultured OVCAR RFP ovarian cancer cell lines. (n=3 wells/concentration tested); $IC_{50}$ at 72 h.=$6.327\times10^{-3}$ µg/mL).

FIG. 1B shows a dosage curve for the TSD-001 paclitaxel liposomal formulation against cultured OVCAR RFP ovarian cancer cell lines. (n=3 wells/concentration tested; $IC_{50}$ at 72 h.=$6.802\times10^{-3}$ µg/mL).

FIG. 1C shows a dosage curve for the TSD-001 paclitaxel liposomal formulation against cultured OVCAR-RFP ovarian cancer cell lines. (n=4 wells/concentration tested; $IC_{50}$ at 72 h.=$7.553\times10^{-3}$ µg/mL).

FIG. 2A shows a dosage curve for the Abraxane® paclitaxel formulation against cultured OVCAR RFP ovarian cancer cell lines. (n=3 wells/concentration tested; $IC_{50}$ at 72 h.=$3.36\times10^{-2}$ µg/mL).

FIG. 2B shows a dosage curve for the Abraxane® paclitaxel formulation against cultured OVCAR RFP ovarian cancer cell lines. (n=4 wells/concentration tested; $IC_{50}$ at 72 h.=$3.308\times10^{-2}$ µg/mL).

FIG. 2C shows a dosage curve for the Abraxane® paclitaxel formulation against cultured OVCAR-RFP ovarian cancer cell lines. (n=4 wells/concentration tested; $IC_{50}$ at 72 h.=$3.301\times10^{-2}$ µg/mL).

FIG. 3A shows a dosage curve for doxorubicin HCl against cultured OVCAR RFP ovarian cancer cell lines. (n=3 wells/concentration tested; $IC_{50}$ at 72 h.=$1.703\times10^{-1}$ µg/mL).

FIG. 3B shows a dosage curve for doxorubicin HCl against cultured OVCAR RFP ovarian cancer cell lines. (n=3 wells/concentration tested; $IC_{50}$ at 72 h.=$1.322\times10^{-1}$ µg/mL).

FIG. 3C shows a dosage curve for doxorubicin HCl against cultured OVCAR RFP ovarian cancer cell lines. (n=4 wells/concentration tested; $IC_{50}$ at 72 h.=$1.66\times10^{-1}$ µg/mL).

DETAILED DESCRIPTION

Figure 1A:
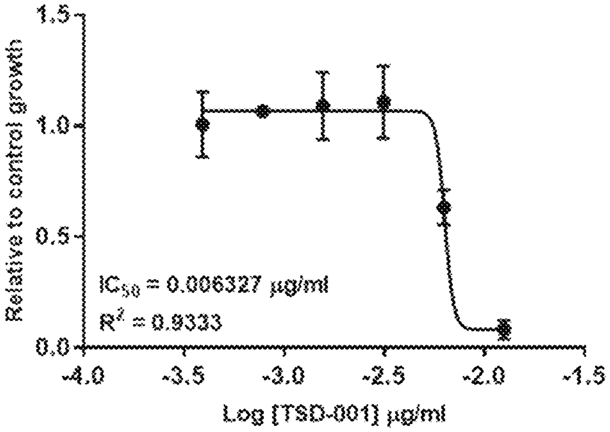
FIGS. 1A-C show the results of triplicate assays, respectively, to determine dosage curves and $IC_{50}$ doses for the TSD-001 paclitaxel liposomal formulation (Pac:DMPC:DMPG=1:1.43:0.567) against cultured OVCAR-RFP ovarian cancer cell lines over a 72 hour time course. The mean $IC_{50}$ dose of the assays in FIGS. 1A-C=$7.449\times10^{-3}\pm9.63\times10^{-4}$ µg/mL.

The invention described herein is directed to treating neoplasms by intraperitonealy administering liposomal formulations of chemotherapeutic drugs. Thus, the invention relates to methods and uses of liposomal formulations of chemotherapeutic drugs to treat neoplasms by contacting cells of the neoplasm with the liposomal formulations, which are administered via intraperitoneal administration. Accordingly, in embodiments of the invention, a liposomal formulation of a chemotherapeutic drug is intraperitoneally-admininistered to a subject, in need thereof, to treat a neoplasm. In such embodiments, the administered liposomal formulation contains an effective amount of the chemotherapeutic drug, which is in contact with the neoplasm for a sufficient period of time, to treat the neoplasm.

Neoplasms. A neoplasm is tissue composed of cells that grow in an abnormal way. Accordingly, neoplastic diseases are characterized by abnormal and uncontrolled cell growth that result in the production of a neoplasm. The term, “neoplasm” is synonymous with the term “tumor”. An individual suffering from a neoplastic disease is defined as having at least one neoplasm. Neoplasms may be benign or malignant. Benign tumors remain localized as a discrete mass. A malignant tumor is metastatic, meaning it can spread to other parts of the body, including via the blood and lymph systems. A system exists to classify malignant tissue according to the degree of malignancy, from grade 1, barely malignant, to grade 4, highly malignant. The term “malignant tumor” is synonymous with the term “cancer”, or the like, such as “cancerous tumor”.

In preferred embodiments, a method of the invention can be used to treat ovarian cancer. Examples of ovarian cancers include, but are not limited to, epithelial ovarian cancer, a malignant sex cord-stromal tumor, a malignant germ cell neoplasm, an ovarian low malignant (LMP) tumor, and a fallopian tube cancer. Accordingly, a method of the invention can be used to treat epithelial ovarian cancer, a malignant sex cord-stromal tumor, a malignant germ cell neoplasm, an ovarian low malignant (LMP) tumor, or a fallopian tube cancer.

In other preferred embodiments, a method of the invention can be used to treat a peritoneal carcinomatosis, which may also be referred to as a “primary peritoneal cancer”. Examples of a peritoneal carcinomatosis include, but are not limited to, carcinomatosis of the ovary, colorectal carcinoma, appendiceal carcinoma, gastric carcinoma, pancreatic carcinoma, peritoneal mesothelioma, mucinous adenocarcinoma, and pseudomyxoma peritonei (“PMP”, a form of cancer characterized by excessive accumulation of mucin, secreted by tumor cells, in the peritoneal cavity). Accordingly, a method of the invention can be used to treat carcinomatosis of the ovary, colorectal carcinoma, appendiceal carcinoma, gastric carcinoma, pancreatic carcinoma, peritoneal mesothelioma, mucinous adenocarcinoma, or PMP.

Indeed, in a preferred embodiment, a method of the invention treats PMP. Pseudomyxoma peritonei (PMP) is a form of cancer characterized by excessive accumulation of mucin, secreted by tumor cells, in the peritoneal cavity. The PMP tumor cells are primarily of appendiceal origin although disseminated cancers of the colon, rectum, stomach, gall bladder, small intestines, urinary bladder, lungs, breast, pancreas and ovary may also contribute to the disease. The mucinous mass that is secreted accumulates in the abdominal cavity causes increased internal pressure on the digestive tract which is associated with significant morbidity and mortality due to nutritional compromise.

Liposomal Formulations. The liposomal formulations of chemotherapeutic drugs that are administered in accordance with the invention are typically prepared by hydrating proliposomal powder dispersions of a chemotherapeutic drug and one or more lipid components, as described in U.S. patent application Ser. Nos. 16/066,836 and 16/348,801, and their respective corresponding PCT applications, WO 2018/089759 and WO 2017/120586, which are all incorporated herein in its entirety.

A chemotherapeutic drug according to the invention is any agent, such as, for example, a small molecule compound, that can be formulated into liposomes composed of phospholipid molecules and, optionally, cholesterol. Phospholipids are molecules that have two primary regions, a hydrophilic head region comprised of a phosphate of an organic molecule and one or more hydrophobic fatty acid tails. Naturally occurring phospholipids generally have a hydrophilic region comprised of choline, glycerol, and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, at, for example, bilayer edges, while, at the same time, minimizing the ratio of surface area to volume, and maintaining a minimal energy conformation, the two lines of phospholipids, known as a phospholipid bilayer or a lamella, converge into a liposome. In doing so, the liposomes entrap aqueous medium, and whatever may be dissolved or suspended in it, in the core of the sphere.

Examples of phospholipids that may be used in a liposomal formulation comprising a chemotherapeutic drug according to the invention include but are not limited to distearoyl phosphatidylcholine (DSPC), dipalmitoyl phosphatidylcholine (DPPC), dimyristoyl phosphatidylcholine (DMPC), egg phosphatidylcholine (egg-PC), soy phosphatidylcholine (soy-PC), dimyrsitoyl phosphatidyl glycerol sodium (DMPG), 1,2-dimyristoyl-phosphatidic acid (DMPA), dipalmitoylphosphatidylglycerol (DPPG), dipalmitoyl phosphate (DPP), 1,2-distearoyl-sn-glycero-3-phospho-rac-glycerol (DSPG), 1,2-distearoyl-sn-glycero-3-phosphatidic acid (DSGPA), phosphatidylserine (PS), and sphingomyelin (SM), or combinations of any of the aforementioned phospholipids.

Liposomes according to the invention typically, but not necessarily, a first and a second phospholipids. For example, in preferred embodiments of the invention, the liposomes contain: (A) a chemotherapeutic agent; (B) DM PC as a first phospholipid; and (C) DMPG as a second phospholipid. For example, a preferred liposomal formulation of the invention can contain the foregoing components (A), (B), and (C) in weight/weight/weight (“w/w”) ratios of (A):(B):(C) ranging from (1):(1.3 4.5):(0.2-1.5), or any ratios therein. Accordingly, in various embodiments, the the w/w ratios among (A):(B):(C) can be (1):(1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5):(0.2, 0.3, 0.4, 0.5, 0.6, 0.7, 0.8, 0.9, 1.0, 1.1, 1.2, 1.3, 1.4, or 1.5), or any ratio therein.

In other preferred embodiments of the invention, the liposomes, in addition to containing: (A) a chemotherapeutic agent; (B) DM PC as a first phospholipid; and (C) DMPG as a second phospholipid, also contain a component (D), cholesterol. For example, in other preferred embodiments, the liposomal formulation of the invention can contain the foregoing components (A), (B), (C), and (D) in w/w ratios of (A):(B):(C):(D) ranging from (1):(1-4.5):(0.1-2.5):(0.1-2.0), or any ratios therein. Accordingly, in various embodiments, the the w/w ratios among (A):(B):(C):(D) can be (1):(1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5):(0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5):(0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0), or any ratio therein.

In various embodiments of the invention, the administered liposome-formulated chemotherapeutic drug is a taxane agent, such as, but not limited to paclitaxel, docetaxel, cabazitaxel, tesetaxel, DJ-927, TPI 287, larotaxel, ortataxel, and DHA-paclitaxel. In preferred embodiments of the invention, liposomes contain (A) a taxane agent; (B) DMPC as a first phospholipid; and (C) DMPG as a second phospholipid.

Preferred embodiments of paclitaxel liposomal formulations of the invention contain: (A) paclitaxel; (B) DM PC as a first phospholipid; and (C) DMPG as a second phospholipid. For example, a liposomal formulation of the invention can contain the foregoing components (A), (B), and (C) in w/w ratios of (A):(B):(C) ranging from (1):(1.3-3.8):(0.2-1.5), or any ratios therein. Accordingly, in various embodiments, the the w/w ratios among (A):(B):(C) can be (1):(1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, or 3.8):(0.2, 0.3, 0.4, 0.5, 0.6, 0.7, 0.8, 0.9, 1.0, 1.1, 1.2, 1.3, 1.4, or 1.5), or any ratio therein. Examples of such paclitaxel formulations include, but are not limited to w/w ratios among (A):(B):(C) of (1):(3.15):(1); (1):(3.20):(1.05); (1):(3.25):(1.10); and in a particularly preferred embodiment, (1):(1.43):(0.567). which may also be described in rounded ratios, like, for example, (1):(1.4):(1.6) or (1):(1.4):(1.567).

Preferred embodiments of docetaxel liposomal formulations of the invention contain: (A) docetaxel; (B) DMPC as a first phospholipid; and (C) DMPG as a second phospholipid. For example, a liposomal formulation of the invention can contain the foregoing components (A), (B), and (C) in w/w ratios of (A):(B):(C) ranging from (1):(1-2):(0.2-0.7), or any ratios therein. Accordingly, in various embodiments, the the w/w ratios among (A):(B):(C) can be (1):(1.0, 1.1, 1.2, 1.3, 1.4, 1.5, 1.6, 1.7, 1.8, 1.9, or 2.0):(0.2, 0.3, 0.4, 0.5, 0.6, or 0.7), or any ratio therein. Examples of such paclitaxel formulations include, but are not limited to w/w ratios among (A):(B):(C) of (1):(3.15):(1); (1):(3.20):(1.05); (1):(3.25):(1.10); and in a particularly preferred embodiment, (1):(1.43):(0.567).

In various other embodiments of the invention, the administered liposome-formulated chemotherapeutic drug is a platinum-based drug, commonly referred to as "platin drugs"), such as, but not limited to cisplatin, which is the common name for Cis-diamminedichloroplatinum(10), and carboplatin. In preferred embodiments of the invention, liposomes contain (A) a platin drug; (B) DMPC as a first phospholipid; and (C) DMPG as a second phospholipid. For example, a liposomal formulation of the invention can contain the foregoing components (A), (B), and (C) in w/w ratios of (A):(B):(C) ranging from (1):(2.5 4.5):(1 2.5), or any ratios therein. Accordingly, in various embodiments, the the w/w ratios among (A):(B):(C) can be (1):(2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5):(1.0, 1.1, 1.2, 1.3, 1.4, 1.5, 1.6, 1.7, 1.8, 1.9, 2.0, 2.1, 2.2, 2.3, 2.4, 2.5), or any ratio therein.

Preferred embodiments of cisplatin liposomal formulations of the invention contain: (A) cisplatin; (B) DMPC as a first phospholipid; and (C) DMPG as a second phospholipid. Thus, a liposomal formulation of the invention can contain the foregoing components (A), (B), and (C) in w/w ratios of (A):(B):(C) of (1):(2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5):(1.0, 1.1, 1.2, 1.3, 1.4, 1.5, 1.6, 1.7, 1.8, 1.9, 2.0, 2.1, 2.2, 2.3, 2.4, 2.5), or any ratio therein. Examples of such cisplatin formulations include, but are not limited to w/w ratios among (A):(B):(C) of (1):(2.7):(1.2); or (1):(2.75):(1.21); or (1):(2.76):(1.22); or (1):(2.77):(1.2); or (1):(2.78):(1.22); or any ratio contained therein.

Other preferred embodiments of cisplatin liposomal formulations of the invention contain: (A) cisplatin; (B) DMPC as a first phospholipid; (C) DMPG as a second phospholipid and (D) cholesterol. For example, a liposomal formulation of the invention can contain the foregoing components (A), (B), (C), and (D) in w/w ratios of (A):(B):(C):(D) of (1):(2.5-4.5):(1-2.5):(0.5-1), or any ratios therein. Thus, a liposomal formulation of the invention can contain the foregoing components (A), (B), (C), (D) in w/w ratios of (A):(B):(C):(D) of (1):(2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5):(1.0, 1.1, 1.2, 1.3, 1.4, 1.5, 1.6, 1.7, 1.8, 1.9, 2.0, 2.1, 2.2, 2.3, 2.4, 2.5):(0.5, 0.6. 0.7. 0.8, 0.9, or 1.0), or any ratio therein. Examples of such cisplatin formulations include, but are not limited to w/w ratios among (A):(B):(C):(D) of (1):(2.7):(1.2):(0.6); or (1):(2.75):(1.21):(0.65); or (1):(2.76):(1.22):(0.7); or (1):(2.77):(1.2):(0.75); or (1):(2.78):(1.22):(0.8); or (1):(2.78):(1.22):(0.9); or any ratio contained therein.

A liposomal formulation according to the invention can also include at least one pharmaceutically acceptable excipient. Exemplary pharmaceutically acceptable excipients include, a cryoprotectant, such as mannitol, starches, lactose (e.g., lactose monohydrate), sucrose, glucose, trehalose, and silicic acid.

Instillation

The liposomal formulations of the present invention are for intraperitoneal use and may be given by methods conventionally used in the art for instillation into the peritoneal cavity. This may be done at surgery, whether it be open or laparoscopic abdominal surgery. Instillation of the liposomal formulations can be performed under hyperthermic, normothermic or isothermic conditions, as deemed appropriate by the administering clinician based on the conventional definitions of those conditions in the art.

Administration of solutions containing the compositions of the invention may, for example, include: (a) Inserting a catheter, such as a Tenckhoff catheter or similar device, through the abdominal wall to terminate with its outlet positioned in the peritoneal cavity at an appropriate site determined by the treating surgeon; (b) Instilling a suitable volume of suitable fluid containing the composition to be used at the concentration determined by the attending clinician; and (c) Allowing the instilled liposomal formulation to dwell for at least 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, or any amount of time therein. In certain embodiments of the invention, the liposomal formulation is instilled into the subject following cytoreductive surgery (CRS) to remove tumors or nodules greater than, for example, about 5.0 mm across. A patient could be brought from the operative theatre following CRS to a post-anaesthesia care unit ("PACU") with an intraperitoneal catheter clamped and ready for the instillation step. Following completion of the intraperitoneal dwell time, the intraperitoneal catheter is opened and the liposome formulation drains from the peritoneal cavity via gravity drainage.

Effective Amount

An effective amount of a chemotherapeutic drug or a liposomal formulation carrying a chemotherapeutic drug, according to the invention described herein is generally that which can exhibit a therapeutic effect to an extent such as to ameliorate the treated disease, disorder, or condition. In other words, an effective amount of a liposomal formulation of the invention that is administered to a subject contains a sufficient dosage amount of a chemotherapeutic drug to have an anti-proliferative therapeutic effect on a neoplasm in the subject. In an embodiment of the invention, the chemotherapeutic drug delivered by the intraperitoneally-admonistered liposomal formulations penetrates deeper than 4 or 5 cell layers beneath the peritoneum to reach tumor cells that are lodged as deep as 2.5 mm below the surface.

In some embodiments, an effective amount of a liposomal formulation described herein can be that amount sufficient to effect a desired result on a cancerous cell or tumor, including, but not limited to, for example, inhibiting metastisis, reducing tumor size, reducing tumor volume, decreasing vascularization of a solid tumor, reducing or eliminating recurrence of a tumor, reduce recurrence of tumor growth, or reduce the number of cancerous cells in the subject. In certain embodiments, an effective amount of a liposomal formulation according to the invention can be the amount that contains a dosage amount of chemotherapeutic drug to results in a percent tumor reduction or inhibition of more than about 55%, about 60%, about 65%, about 70%, about 75%, about 80%, about 85%, about 90%, about 95%, about 99%, or about 100%. Tumor reduction can be determined by a variety of methods known in the art, such as, for example, by measuring the dimensions of tumor(s) upon removal from the subject, e.g., using calipers, or while in the body using imaging techniques, e.g., ultrasound, computed tomography (CT) or magnetic resonance imaging (MRI) scans.

With respect to ovarian cancer, the cell marker, Cancer Antigen 125 ("CA-125"), is the most frequently used biomarker for ovarian cancer detection. (Nossov et al.) Indeed, around 90% of women with advanced ovarian cancer have elevated levels of CA-125 in their blood serum, making CA-125 a useful tool for detecting ovarian cancer after the onset of symptoms. (Gupta D et al.) Therefore, Monitoring CA-125 blood serum levels is also useful for determining how ovarian cancer is responding to treatment (with the duration of disease-free survival correlating with the rate of fall of CA-125) and for predicting a patient's prognosis after treatment. (Bast R C et al. and Gocze P et al.). Accordingly in some embodiments of the invention, an effective amount of an intraperitoneally-administered liposomal formulation of the invention correlates to the amount associated with a CA-125 half-life of less than 20 days relative to pre-treatment baseline CA-125 levels.

Furthermore, the effective amount of a liposomal formulation or chemotherapeutic drug described herein will vary depending upon the subject treated. Indeed, the specific therapeutically effective dose level for any particular subject will depend upon a variety of factors including: the neoplasm being treated and the severity of the neoplastic disorder; activity of the specific chemotherapeutic drug employed; the specific composition employed; the age, body weight, general health, sex and diet of the patient; the time of administration; the duration of the treatment; drugs used in combination or coincidental with the specific chemotherapeutic drug employed; and like factors well known in the medical arts.

Intraperitoneal administration of liposomal formulations described herein can occur as a single event, a periodic event, or over a time course of treatment. For example, the liposomal formulations can be administered one time, weekly for 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks. As another example, the liposomal formulations can be administered every 1 to 9 weeks, every 2 to 9 weeks, every 3 to 9 weeks, every 4 to 9 weeks, every 5 to 9 weeks, every 6 to 9 weeks, every 7 to 9 weeks, every 8 to 9 weeks, every 2 weeks, every 3, weeks, every 4 weeks, every 5 weeks, every 6 weeks, every 7 weeks, every 8 weeks, or every 9 weeks. One of ordinary skill, such as a clinician, will understand these regimes to be exemplary and could design other suitable periodic regimes. For example, a liposomal formulation according to the invention can be administered performed 1 month, 2 months, 3 months, 4 months, 5 months, 6 months, 7 months, or 8 months following the last treatment according to the invention.

Kits

A liposomal formulation according to the invention, either in liquid or powdered form, can be provided in a kit suitable for delivering liposomal formulations described herein via intraperitoneal instillation. Such kits can be in the form of a closed package system, containing the liposomal formulation and an intraperitoneal catheter, and, in certain embodiments, instructions for administration. When supplied as a kit, reagents can be provided in separate containers such as, for example, sterile water or saline to be added to a lyophilized, or other type of proliposomal form of the liposomal formulation component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like. In certain embodiments, kits can also be supplied with instructional materials. Instructions may be printed on paper or other substrate, or may be supplied as an electronic-readable medium. Detailed instructions may not be physically associated with the kit; instead, a user may be directed to an Internet web site specified by the manufacturer or distributor of the kit.

Examples

Example 1. Determination of paclitaxel $10_{50}$ in TSD-001-treated human ovarian cancer cells. A sulforhodamine B (SRB) assay-based approach was employed to determine the inhibitory concentration $(IC)_{50}$ of paclitaxel against OVCAR3-RFP human ovarian cancer cells (Anticancer Inc.) treated with the TSD-001 paclitaxel liposomal formulation (Paclitaxel:DMPC:DMPG=1:1.43:0.567). For use in the assay, lyophilized TSD-001 was reconstituted in sterile injectable-grade water to a concentration of 6 mg/mL and subsequently serially diluted in RPMI cell culture medium (RPMI-1640 with L-glutamine, Corning). Three separate dosage curve assays were performed. In two of the assays, the serial dilutions of TSD-001 ranged from 0.05 μg/mL to 0.391 ng/mL, and in the third assay, the serial dilutions of TSD-001 ranged from 0.0128 μg/mL to 2.147 ng/mL.

Serial dilutions of the Abraxane® paclitaxel formulation (nanoparticle albuminbound paclitaxel) and doxorubicin HCl were also prepared to perform comparative dosage curve assays in OVCAR3-RFP cells. For these assays, lyophilized Abraxane® was dissolved in RPMI medium to a concentration of 1 mg/mL, and doxorubicin HCl was dissolved in a small amount of DMSO, and the diluted in RPMI medium to a concentration of 1 mg/mL. Three separate dosage curve assays were performed for Abraxane®. In one assay, the serial dilutions of Abraxane® ranged from 0.04 μg/mL to 0.078 ng/mL. In the second assay, the serial dilutions of Abraxane® ranged from 0.04 μg/mL to 8.39 ng/mL and in the third assay, the serial dilutions of Abraxane® ranged from 0.032 μg/mL to 8.39 ng/mL. Three separate dosage curve assays were also performed for doxorubicin HCl. In one assay, the serial dilutions of doxorubicin HCl ranged from 0.8 μg/mL to 6.4 ng/mL. In the second assay, the serial dilutions of doxorubicin HCl ranged from 1 μg/mL to 0.013 ng/mL and in the third assay, the serial dilutions of doxorubicin HCl ranged from 0.5 μg/mL to 67.11 ng/mL.

Figure 1B:
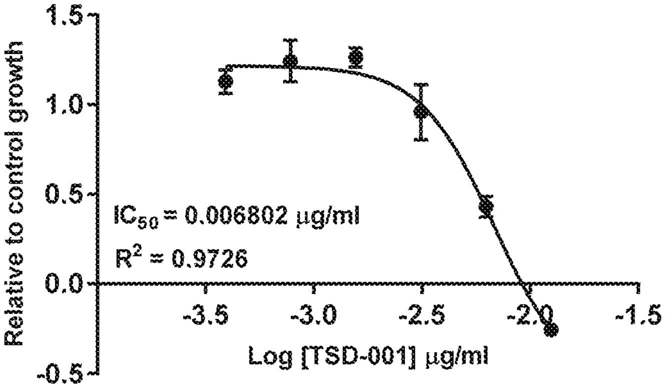
Figure 1C:
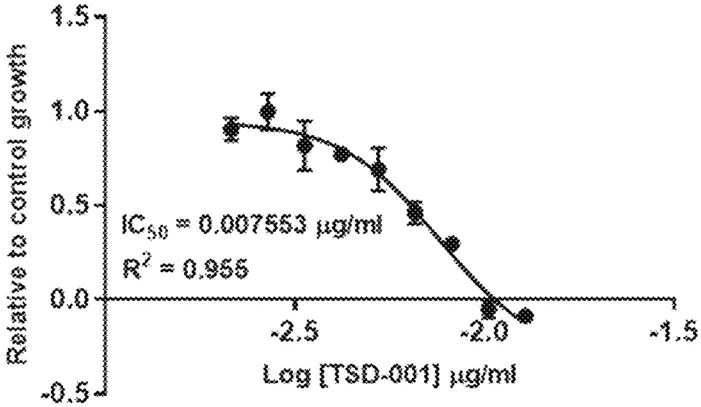
Figure 2A:
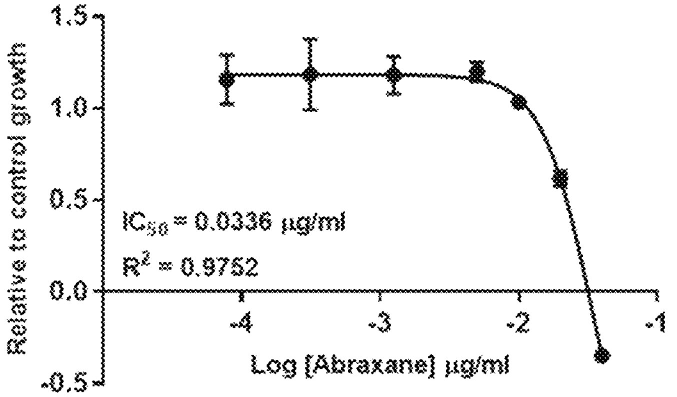
FIGS. 2A-C show the results of triplicate assays, respectively, to determine dosage curves and $IC_{50}$ doses for the Abraxane® paclitaxel formulation (nanoparticle albumin-bound paclitaxel) against cultured OVCAR-RFP ovarian cancer cell lines over a 72 hour time course. The mean $IC_{50}$ dose of the assays in FIGS. 2A-C=$3.322\times10^{-2}\pm2.21.\times10^{-3}$ µg/mL.
Figure 2B:
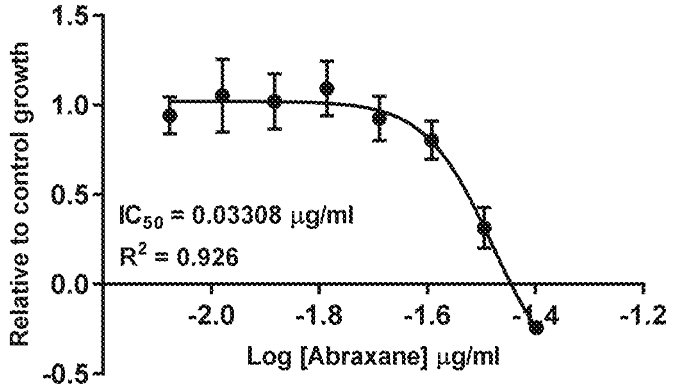
Figure 2C:
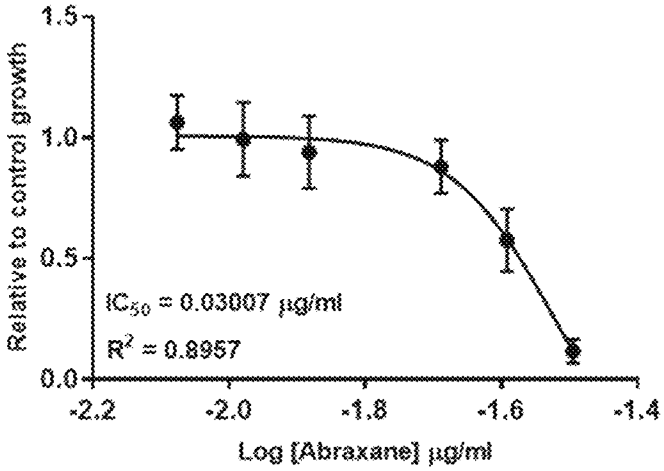
Figure 3A:
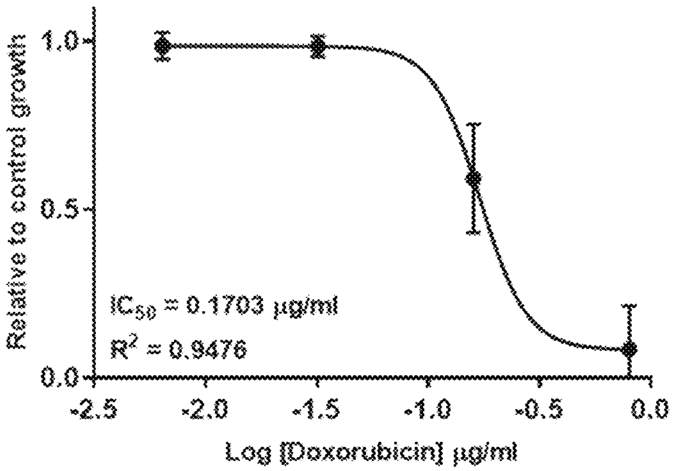
FIGS. 3A-C show the results of triplicate assays, respectively, to determine dosage curves and $IC_{50}$ doses for doxorubicin HCl against cultured OVCAR RFP ovarian cancer cell lines over a 72 hour time course. The mean $IC_{50}$ dose of the assays in FIGS. 3A-C=$1.910\times10^{-1}\pm8.353.\times10^{-2}$ µg/mL.
Figure 3B:
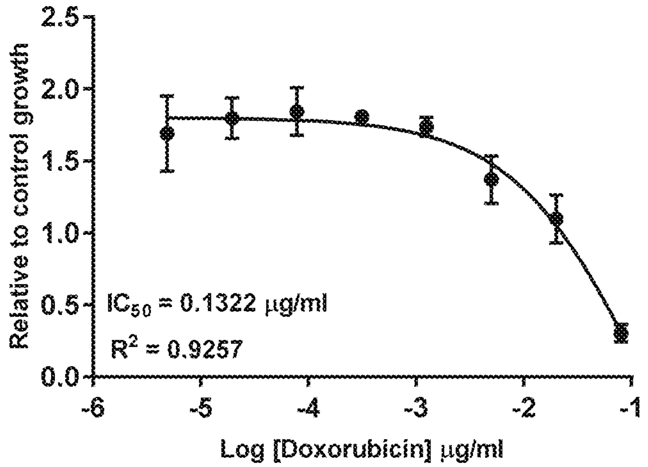
Figure 3C:
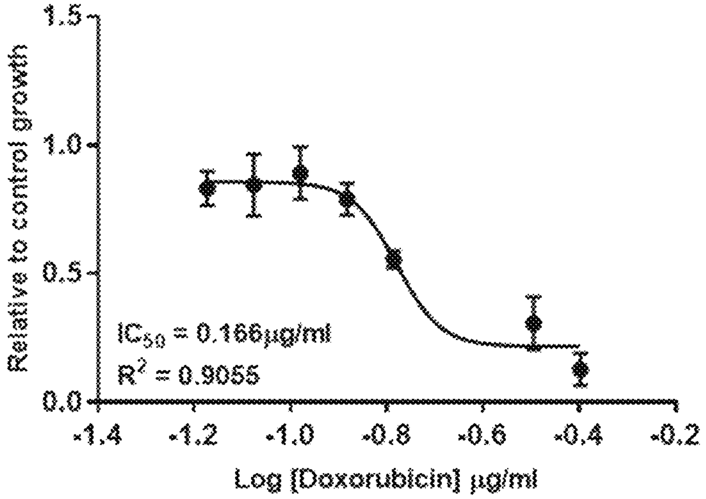

OVCAR3-RFP cells were seeded onto 96-well clear flat-bottom polystyrene tissue culture plates (Corning) at a density of approximately $5\times10^3$ cells/well in 200 μl of RPMI. The cells were incubated at 37° C. and 5% $CO_2$ until the cells attached to the well surfaces completely. The serially diluted TSD-001, Abraxane®, and doxorubicin HCl preparations were added to wells in triplicate or quadruplicate as indicated in the Fig. legends for 1A-C, 2A-C, and 3A-C in the Brief Description of Drawings of this disclosure. After a 72 h treatment period with the formulations, the media were aspirated. The treated cells were fixed by gently adding 100 μl of 10% trichloroacetic acid (TCA) into each well, and incubating the plates at 4° C. for 1 hour. After incubation, the plates were washed with tap water 4 times, without streaming the water directly into the wells. The plates were then tapped gently on paper towels, and air-dried at room temperature. After drying, 100 μl of 0.057% (w/v) SRB solution (SRB in 1% acetic acid) was added to each well. The plates were incubated at room temperature in the SRB solution for 30 minutes, and then quicky rinsed 5 times with 1% acetic acid to remove unbound dye, and then, air-dried at room temperature. Protein-bound SRB was detected by adding 200 μl 10 mM Tris base solution (pH 10.5) to each well, followed by placing the plate(s) on a byratory shaker for 5 minutes to allow the Tris solution to solubilize SRB. The plates were read using a microplate reader at an absorbance of 510 nm. The results for the foregoing assays are reported in FIGS. 1A-C (TSD-001), 2A-C (Abraxane®), and 3A-C (doxorubicin).

Table 1 contains the mean IC50 values calculated from the combined data for the TSD-001, Abraxane®, and doxorubicin assays described above, respectively.

TABLE 1

| Formulation assayed | Mean $IC_{50}$ (μg/mL) against OVCAR3-RFP cells (n ≥ 5) |
|---|---|
| TSD-001 (TesoRx) | 0.007449 ± 0.000963 |
| Abraxane ® (Celgene) | 0.033224 ± 0.002213 |
| Doxorubicin HCl (Alfa Aesar) | 0.190917 ± 0.083525 |

REFERENCES

Armstrong D K et al. Intraperitoneal cisplatin and paclitaxel and ovarian cancer. NEJM 2006; 354:34-43

Bast R C, Klug T L, St John E, Jenison E, Niloff J M, Lazarus H, Berkowitz R S, Leavitt T, Griffiths C T, Parker L, Zurawski V R, Knapp R C (October 1983). "A radioimmunoassay using a monoclonal antibody to monitor the course of epithelial ovarian cancer". *The New England Journal of Medicine.* 309 (15): 883-7. doi:10.1056/NEJM198310133091503, PMID 6310399.

Dedrick R L. Theoretical an experimental bask of intraperitoneal chemotherapy. Semin Oncol 1935: 12: suppl 4:1-6.

Göcze P, Vahrson H (April 1993). "[Ovarian carcinoma antigen (CA 125) and ovarian cancer (clinical follow-up and prognostic studies)]". *Orvosi Hetilap* (in Hungarian). 134 (17): 915-8. PMD 84797:36.

Gupta D, Lis C G (2010). "Pretreatment serum albumin as a predictor of cancer survival: a systematic review of the epidemiological literature". *Nutrition Journal.* 9: 69, doi:10.1186/1475-2891-9-69. PMC 3019132 Freely accessible. PMD 21176210.

Nossov V, Amneus M, Su F, Lang J Janco J M, Reddy S T, Farias-Eisner R (September 2008). "The early detection of ovarian cancer: from traditional methods to proteomics. Can we really do better than serum CA-125*?"*. *American Journal of Obstetrics and Gynecology.* 199 (3): 215-23.

Willemien J. van Driel, et al. "Hyperthermic Intraperitoneal Chemotherapy in Ovarian Cancer". *New Eng. J. of Med.* 378:230-240.

The claimed invention is:

1. A method of treating a neoplasm in a subject comprising intraperitoneally instilling in the subject a liposomal formulation comprising liposomes, wherein the liposomes consist of:

(a) a taxane drug;

(b) dimyristoyl phosphatidylcholine (DMPC); and (c) dimyristoyl phosphatidyl glycerol sodium (DMPG), wherein the weight/weight/weight (w/w/w) ratios of (a):(b):(c) are (1):(1.3-4.5):(0.4-2.5), for a sufficient intraperitoneal dwell time and in an effective amount to inhibit growth of the neoplasm, wherein the neoplasm is an ovarian cancer neoplasm, a malignant sex cord-stromal tumor, carcinomatosis neoplasm of the ovary, a malignant germ cell neoplasm, an ovarian low malignant (LMP) tumor, a fallopian tube cancer neoplasm, or a primary peritoneal cancer neoplasm.

2. The method of claim 1, wherein the taxane drug is paclitaxel, docetaxel, cabazitaxel, tesetaxel, DJ-927, TPI 287, larotaxel, ortataxel, or DHA-paclitaxel.

3. The method of claim 2, wherein the taxane drug is paclitaxel.

4. The method of claim 3, wherein the (a) paclitaxel, (b) DMPC, and (c) DMPG are at w/w/w ratios of (a):(b):(c) of (1):(1.3-2):(0.4-0.7).

5. The method of claim 4, wherein the (a) paclitaxel, (b) DMPC, and (c) DMPG are at w/w/w ratios of (a):(b):(c) of (1):(1.4):(0.6).

6. The method of claim 2, wherein the taxane drug is docetaxel.

7. The method of claim 6, wherein the (a) docetaxel, (b) DMPC, and (c) DMPG are at w/w/w ratios of (a):(b):(c) of (1):(1.3-2):(0.4-0.7).

8. The method of claim 1, wherein the intraperitoneal dwell time is from 15 minutes to 12 hours.

9. The method of claim 8, wherein the liposomal formulation is drained from the peritoneal cavity via gravity drainage.

10. The method of claim 1, wherein the method is performed at least every 1 to 9 weeks, performed weekly for 1 to 20 weeks, performed subsequently 2 to 8 months following the last treatment, and/or performed at the completion of cytoreductive surgery.

11. The method of claim 1, wherein the subject also receives intravenous chemotherapy.

12. The method of claim 1, wherein the intraperitoneal instillation of the liposomal formulation is performed using a closed package system, comprising the liposomal formulation and an intraperitoneal catheter.

13. The method of claim 1, wherein the intra peritoneal instillation of the liposomal formulation is performed under hyperthermic, normothermic or isothermic conditions.

14. A kit comprising the closed package system of claim 12.

* * * * *